United States Patent [19]

Waggoner

[11] Patent Number: 5,709,546
[45] Date of Patent: Jan. 20, 1998

[54] WATER SANITIZING SYSTEM AND PROCESS

[76] Inventor: Mark B. Waggoner, 7515 White Castle La., Plano, Tex. 75025

[21] Appl. No.: 755,573

[22] Filed: Nov. 27, 1996

[51] Int. Cl.$^6$ ................................................ A61C 1/10
[52] U.S. Cl. .......................... 433/82; 433/84; 433/98
[58] Field of Search ............................ 433/82, 84, 85, 433/86, 87, 88, 98, 99

[56] References Cited

U.S. PATENT DOCUMENTS

| | | | |
|---|---|---|---|
| 4,540,504 | 9/1985 | Eoga | 510/117 |
| 4,647,458 | 3/1987 | Ueno et al. | 424/128 |
| 4,847,088 | 7/1989 | Blank | 424/404 |
| 5,055,043 | 10/1991 | Weiss et al. | 433/86 |
| 5,087,198 | 2/1992 | Castellini | 433/80 |
| 5,158,454 | 10/1992 | Viebahn et al. | 433/82 |
| 5,199,604 | 4/1993 | Palmer et al. | 433/32 |
| 5,230,624 | 7/1993 | Wolf et al. | 433/82 |
| 5,295,829 | 3/1994 | Frey et al. | 433/82 |
| 5,318,443 | 6/1994 | Overmyer | 433/104 |
| 5,494,112 | 2/1996 | Arvidson et al. | 169/13 |
| 5,512,200 | 4/1996 | Garcia | 252/142 |
| 5,526,841 | 6/1996 | Detsch et al. | 137/15 |

OTHER PUBLICATIONS

Center for Disease Control and Prevention: Recommended infection–control practices for dentistry, 1993. *MMWR* 42:No. RR–8–7, 1993.

B. G. Shearer, "Biofilm and the dental office," *Journal of the American Dental Association*, vol. 127, No. 2, 1996.

Waggoner, M.B., "The New CDC Surgical Water Recommendations: Why They Should Be Implemented and What They Require," *Compendium*, vol. 17, No. 6, Jun. 1996.

D'Aquino, M., "Lemon Juice as a Natural Biocide for Disinfecting Drinking Water," *Bulletin of PAHO* 28(4), 1994.

J. F. Williams, et al, in "Microbial Contamination of Dental Unit Waterlines: Prevalence, Intensity and Microbiological Characteristics," *The Journal of the American Dental Association*, vol. 124, No. 10, 1993.

R. W. Vess in "The colonization of solid PVC surfaces and the acquisition of resistance to germicides by water microorganisms," *Journal of Applied Bacteriology*, vol. 74, No. 2, 1993.

Anderson et al, "Effect of Disinfectants on Pseudomonades Colonized on the Interior Surface of PVC Pipes," *American Journal of Public Health*, vol. 80, No. 1, pp. 17–21.

Costerton et al, "Microbial Biofilms," *Annual Review of Microbiology*, vol. 49, 1995.

*Primary Examiner*—John J. Wilson
*Attorney, Agent, or Firm*—William D. Jackson; Locke Purnell Rain Harrell

[57] ABSTRACT

A method for incorporating concurrent delivery of a bactericidal agent into water intended for supply to a dental unit. A reservoir adapted to contain a liquid bactericidal agent is connected to a variable rate pump having an inlet line extending from the reservoir to the inlet of the pump. An outlet line extends from the pump outlet and provides a bactericide supply line. A water supply line is adapted to be connected to a source of water under pressure which provides a flow path through the system to a suitable outlet adapted to be connected to a dental unit. A mixing junction interconnects the water supply line and the bactericide supply line so that bactericide can be mixed into the water supply line. A flow sensing unit is responsive to fluid flow in the water supply line and generates an output parameter representative of this flow rate. A flow control system responds to this measured parameter to vary the pumping rate of the pump. An enlarged mixing chamber is located between a mixing junction and the water supply line outlet with the sensing unit interposed between the mixing chamber and the mixing junction. A water filter is interposed between the water supply line between the inlet thereof and the mixing junction. Check valves are located in the water supply line upstream downstream of the mixing junction. The mixing chamber is interposed between the second check valve and the outlet of the supply line.

48 Claims, 3 Drawing Sheets

WATER SANITIZING SYSTEM AND PROCESS

FIELD OF THE INVENTION

This invention relates to methods and systems for the provision of sanitized water to medical utilization devices such as dental units and the like and treatment of the internal water contact surfaces with said sanitized water.

BACKGROUND OF THE INVENTION

The presence of pathogens in the water to be used in medical applications is naturally to be avoided whenever possible. This is especially important in so-called invasive procedures involving a surgical entry into tissues of the patient during various medical and dental treatments. One potential source of serious and sometimes even life-threatening infections can be found in instrument centers, commonly referred to as "dental units," which provide the various instruments, such as drill motors, irrigators, and the like used in dental treatments. The Center for Disease Control and Prevention (CDC) has issued recommendations in effect for the past four years which apply to water to be supplied to dental units during invasive procedures often encountered in dental treatments. (Center for Disease Control and Prevention: Recommended infection-control practices for dentistry, 1993. *MMWR* 42: No.RR-8:7, 1993.). According to B. G. Shearer in "Biofilm and the dental office," *Journal of the American Dental Association*, Vol. 127, No. 2, 1996, the American Dental Association has set forth goals for the year 2000 whereby all water delivered to dental patients will have no more than 200 colony forming units (CFU) of live bacteria per cubic milliliter. These recommendations and their application to dentistry are discussed in Waggoner, M. B., "The New CDC Surgical Water Recommendations: Why They Should Be Implemented and What They Require," *Compendium*, Vol. 17, No. 6, June 1996. As discussed there, dental water line contamination has been a longstanding problem. Various studies have shown bacterial colony-forming unit (CFU) levels in dental unit water lines ranging from 10,000 to $100 \times 10^6$ CFU per milliliter. This is due to the accumulation of bacterial colonies lining the internal dental unit tubing and the associated delivery tubing. These colonies are known as bacterial biofilms and are relatively resistant to most known biocidal agents. They act as the source for the majority of the bacterial contamination in dental unit water lines. Thus, even if sterile water, such as saline solutions and the like, are supplied to dental units, the water can become contaminated, resulting in the risk of infection to the patient.

Various procedures and treatments are known in the art for controlling various bacterial disease agents in water used for human consumption and in various medical procedures. Chlorination of domestic drinking water has controlled pathogen levels and is, of course, a well established procedure. Even with chlorination, however, a small but acceptable number of bacteria will survive. In several industries, water system design allows accumulation and growth of these few bacteria. This accumulation and growth is exacerbated if the chlorine, which is actually a gas, is allowed to escape from the water while it is not actively flowing. This chlorine loss rapidly occurs through small bore tubing made of plastic, as is commonly seen in dentistry.

Common alternative to chlorination include heavy metals like copper and silver, iodine, ultraviolet light and ozone and ozone-producing products like peroxide. One relatively unexplored approach is the utilization of high concentrations of citrus juice, such as lemon juice or citric acid as discussed in D'Aquino, M., "Lemon Juice as a Natural Biocide for Disinfecting Drinking Water," Bulletin of PAHO 28(4), 1994. Thus, D'Aquino et al discloses the use of organic acid substances mixed with previously untreated water samples, the substances including natural lemon juice, bottled commercial lemon concentrate, and 7% citric acid solution. Different concentrations of lemon juice and the 7% citric acid solution to natural underground water levels were tested. In general, samples inoculated with the pathogen V-cholerae were not disinfected by 1% lemon juice concentrations in any dilutions resulting in a Ph of 3.9 or higher. As further disclosed by D'Aquino, higher concentrations of 10–25% lemon juice were found to disinfect the water within a period of 5–10 minutes. Lower concentrations down to a minimum of 2% were found to require at least 30 minutes to disinfect the contaminated water.

Various other bactericidal agents, employing both organic and inorganic acids which are useful in forming anti-microbial formulations, are well known in the art. For example, U.S. Pat. No. 4,647,458 to Ueno et al discloses bactericidal agents incorporating mixtures of organic and inorganic acids in alcohol solutions disclosed as useful for bactericides for food stuffs and food processing machines and utensils. Disclosed in Ueno et al are various formulations incorporating organic acids such as lactic acid, acetic acid, tartaric acid, gluconic acid, citric acid, ascorbic acid, malic acid, succinic acid, fumaric acid and phytic acid in combination with various inorganic acids such as phosphoric acid, nitric acid, sulfuric acid, and hydrochloric acid. The salts of such acids also may be employed. The acid or acid salts can be employed in combination with an alcohol, such as ethyl alcohol, in aqueous solutions having a Ph of about 4 or less. U.S. Pat. No. 4,847,088 to Blank discloses an anti-microbial agent comprising a quaternary ammonium silane in combination with an organic acid such as citric acid or maleic acid or an inorganic acid such as boric acid. Various other acids disclosed for use in the Blank formulation include ascetic, adipic, anisic, benzoic, boric, butyric, capric, citraconic, cresotinic, elaidic, formic, fumaric, gallic, glutaric, glycolic, lactic, lauric, levulinic, malic, malonic, oleic, oxalic, palmitic, phthalic, propionic, pyruvic, salicylic, stearic, succinic, tannic, and tartaric acids. The Blank formulations can be used in various carders to treat substrate surfaces such as carpet fabrics, upholstering, furniture, and the like.

Another application of bactericides is in the treatment of water, such as chlorinated city water and the like, which is applied for use in dental instruments. As discussed in the aforementioned paper by Waggoner, the bacterium *Pseudomonas aeruginosa* is commonly encountered in water supplied to dental units along with the various other microbes including *Burkolacea cepacia*, Legionella species, *Klebsiella pneumoniae*, Staphylococcus species, Streptococcus species, and *Escherichia coli*. As noted in U.S. Pat. No. 5,158,454 to Viebahn, a singular disinfection and sterilization of the water is ineffective since the infectious microbes are resupplied in the course of the dental operation from the city water or from the patient. In the Viebahn system, a strong oxidant or ozone is incorporated into water in several water reservoirs and passed from there to suitable water supply lines such as those used by a dentist or a dental assistant in the operation of the various dental instruments of a dental unit. The ozone level is maintained initially high to provide the desired disinfectant action in the water while at the same time providing an ozone level which is zero or near zero for the water at the various discharge points where the patient is contacted, such as a syringe or a drill. An ozone detector can be used to sense the ozone level when applied to various end point devices with a signal representative of ozone concentration applied to a control unit which then provides feedback signal for control of the ozone level in a ozone-producing device. Thus, the ozone level is maintained sufficiently high when supplied to one or more water reservoirs to provide for effective control of undesirable microbes and then reduced, if necessary, through the addition of ozone converters as the water is supplied to the various end point devices.

Another system desired to control the presence of infectious microbes in water supplied to dental units is disclosed is U.S. Pat. No. 5,230,624 to Wolf et al. Here, an in-line filter is provided in a supply line leading to a dental instrument, such as a drill or the like, and contains a polyiodide purification resin. The resin functions to neutralize and kill bacteria by the release of iodine from the resin surface to the bacteria through a demand release process involving electrostatic attraction. The resin is positively charged such that the negatively-charged microorganisms are attracted to the resin to the point where iodine is released directly into the microorganism.

Yet another system for delivering treated water to dental handpieces and the like is disclosed in U.S. Pat. No. 5,199,604 to Palmer. In Palmer, a plurality of solution reservoirs are connected through a valved manifold to the inlet side of a peristaltic pump which supplies suitable handpieces, such as an irrigator, for treatment of periodontal disease. By way of example, the various reservoirs may contain colored-coded solutions, such an orange color for a bacteriostatic rinse solution and another color for a hydrogen peroxide solution and various other colors for additional solutions used for irrigation purposes. The peristaltic pump can be employed to deliver the particular irrigating solution selected at a substantially constant pressure and a substantially constant flow rate.

Methods utilized to eliminate bacterial biofilms in industry include steam purging and hyperchlorination "shock treatments." In dentistry, hyperchlorination "shock treatments" have been used, but the "shock treatments" must be repeated every week because the biofilm begins to regrow in that period of time. This type of system also requires use of only sterile water to slow down the biofilm formation. According to J. F. Williams, et al, in "Microbial Contamination of Dental Unit Waterlines: Prevalence, Intensity and Microbiological Characteristics," *The Journal of the American Dental Association*, Vol. 124, No. 10, 1993, mature biofilms are notoriously resistant to chemical disinfection including these "shock treatments." Thus, if a practitioner does not treat his system for several weeks, the biofilm will become resistant to this method. According to Vess et al in "The colonization of solid PVC surfaces and the acquisition of resistance to germicides by water micro-organisms," *Journal of Applied Bacteriology*, Vol. 74, No. 2, 1993, most biocidal agents have not been shown to destroy a mature biofilm.

SUMMARY OF THE INVENTION

In accordance with the present invention, there is provided a system for incorporating concurrent delivery of a bactericidal agent into water intended for supply to a dental unit. The system of the present invention comprises a reservoir adapted to contain a liquid bactericidal agent and a variable rate pump having an inlet line extending from the reservoir to the inlet of the pump. An outlet line extends from the pump outlet and provides a bactericide supply line. The system further comprises a water supply line adapted to be connected to a source of water under pressure which provides a flow path through the system to a suitable outlet adapted to be connected to a dental unit or the like. A mixing junction interconnects the water supply line and the bactericide supply line so that bactericide can be mixed into the water supply line. The system further comprises a flow sensing unit which is responsive to fluid flow in the water supply line and generates an output parameter representative of this flow rate. A flow control system responds to this measured parameter to vary the pumping rate of the pump.

In a preferred embodiment of the invention, the mixing junction is upstream of the sensing unit and the pump is a peristaltic pump. The system further comprises an enlarged mixing chamber between the mixing junction and the water supply line outlet, and in this embodiment the sensing unit preferably is interposed between the mixing chamber and the mixing junction. A water filter, which preferably is at least a 50 micron filter, is interposed between the water supply line between the inlet thereof and the mixing junction.

In yet a further aspect of the invention, the system comprises check valves in the water supply line. One check valve is disposed in the line upstream of the mixing junction. A second check valve is disposed in the line downstream of the mixing junction. In this embodiment of the invention the enlarged mixing chamber is preferably interposed between the second check valve and the outlet of the supply line adapted to be connected to the dental unit.

In a further embodiment of the invention, there is provided a process for supplying the relatively bacteria-free aqueous medium to a dental unit. In carrying out this process, a stream of water is supplied to the dental unit and applied from the dental unit through a suitable end device such as a drill irrigator or the like into the patient's mouth. A hydroxycarboxylic acid is incorporated into the stream of water supplied to the dental unit. In concentrations typically delivered to the dental drill and the ultrasonic scaler, this acid/water mixture has been shown to reduce *Pseudomonas aeruginosa* and *Escherichia coli* bacteria from a 140,000,000 CFU per milliliter level to 0 CFU in 10 minutes. Other bacteria, *Staphylococcus aureus*, took greater than 10 minutes but less than 30 minutes to see a reduction of 190,000,000 CFU per milliliter down to 0. The flow rate of water supplied to the dental unit is sensed, and the rate of incorporation of the hydroxycarboxylic acid into the water is adjusted in response to the sensed flow rate.

In another embodiment of the invention, there is provided a process for supplying a medium which is capable of eliminating a mature bacterial biofilm in a presently contaminated system. In carrying out the process, a hydroxycarboxylic acid is concurrently incorporated into the water supplied for the dental unit. The continuous contact of the acid/water medium to the biofilm has been shown to completely destroy a mature biofilm.

DETAILED DESCRIPTION OF THE INVENTION

Figure 1:
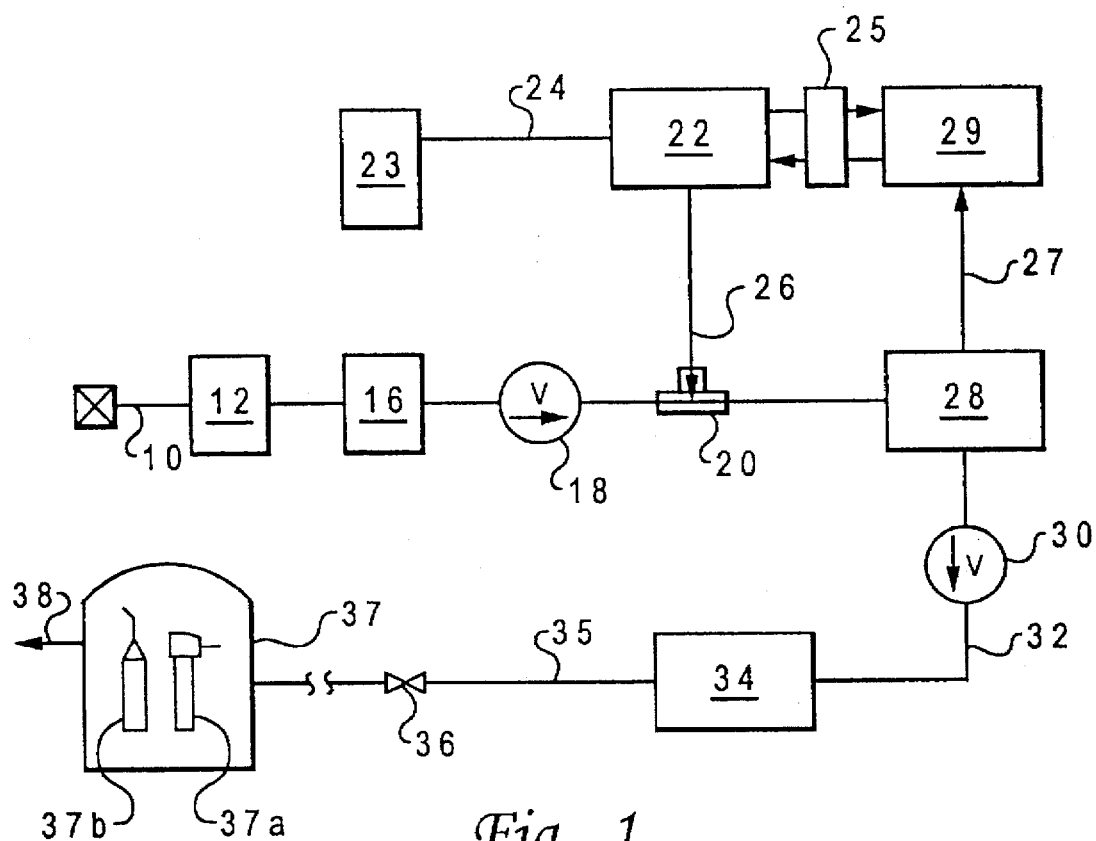
FIG. 1 is a schematic illustration of one embodiment of the invention.

The present invention provides for the treatment of water flowing in water supply lines in a manner to reduce bacterial contamination to a level suitable for human interaction when performing standard dental procedures and the like. In the present invention a bactericide is continuously supplied to a water supply system, such as in a dental unit water line, in a concentration which is acceptable to provide for potable and palatable water, while at the same time eliminating the formation of biofilm by bacteria which are commonly encountered in water sources such as municipal water and bacteria from human sources. As discussed in the aforementioned paper by Waggoner, bacterial contamination in dental unit water lines has been a long recognized problem. CFU levels up to $10 \times 10^6$ ml have been observed. The contamination can stem from municipal water sources or other water supplied to the system or, in the case of dentistry, from the patient because of backflow of patient materials into the dental handpiece which can occur under a number of circumstances.

Chronic contamination of dental unit water lines and the like is due to the buildup of a slime layer, commonly referred to as a bacterial biofilm, resulting most commonly from gram-negative bacteria typically found in municipal water sources. The biofilm itself, and not the municipal water, is the major source of bacterial contamination. The biofilm acts to provide a protective environment for the gram-negative bacteria or for any other pathogenic organisms which can reside in the water being supplied to the unit or for bacteria found in patient materials sucked back into the system.

This invention proceeds in a manner contrary to those prior art procedures discussed above. Rather than attempting to suppress bacterial contamination through strong disinfectants or antioxidants or by periodic application of bactericides to shock the system, the present invention supplies a bactericidal agent in a more or less continuous fashion and at a low concentration which is not likely to cause damage to soft tissue or otherwise be harmful to a patient. The present invention enables the use of bactericides, such as hydroxycarboxylic acids, in low concentrations which are consistent with water to be used in dental or hospital applications or in various regulated products, such as cosmetics, pharmaceuticals, and the like, intended for human consumption or application to tissues.

As noted previously, mature biofilms are established bacterial colonies which are much more difficult to treat than water-born free bacteria. For example, as disclosed in the aforementioned paper by Vess et al, bactericides such as free chlorine in a concentration of only a few parts per million are well-known bactericides which readily kill water-born bacteria. However, such bactericides are recognized to be ineffective in killing mature biofilms. Mature biofilms can generally be characterized as relatively thick colonies of bacterial cells and extracellular material which usually have thicknesses within the range of about 20–60 microns and more particularly within the range of about 30–50 microns. Such mature biofilms and their characteristic resistance to bactericidal attack are discussed in the aforementioned papers by Vess et al and Williams et al and also in papers by Anderson et al, "Effect of Disinfectants on Pseudomonades Colonized on the Interior Surface of PVC Pipes," *American Journal of public Health*, Vol. 80, No. 1, pp. 17–21, and Costerton et al, "Microbial Biofilms," *Annual Review of Microbiology*, Vol. 49, 1995, pp. 711–745. For example, the paper by Anderson et al, in addressing research on mature biofilms resulting from colonies of *Pseudomonas aeruginosa* and *Pseudomonas pickettii*, discusses the survival of biofilm colonies in the presence of various disinfectants ranging from alcohols and aldehydes to quaternary ammonium compounds and halogen-based antiseptics. As discussed there, survivability is attributed to the existence of extra-cellular glycocalyx-like structures which function to protect the embedded bacteria from the action of the antiseptic material. The paper by Costerton et al characterizes mature biofilms as matrix-enclosed bacterial populations which are adherent to each other and/or to surfaces or interfaces. They are described in Costerton et al as being characterized by the production of extensive networks of highly hydrated exopolysaccharides which are characterized as having substantially enhanced resistance to antimicrobial agents. As discussed in Costerton et al, biofilms cells can be characterized as being at least 500 times more resistant to antibacterial agents than free planktonic cells. For a further description of mature biofilms and their characteristics, reference is made to the aforementioned papers by Anderson et al, Vesset al, Williams et al, and Costerton et al, the entire disclosures of which are incorporated herein by reference.

Thus, to the extent a mature biofilm in a system, such as a water delivery system to a dental patient, can function as an ever replenishing reservoir of bacteria, the present invention attacks not only the water-born bacteria but, more importantly, the biofilm bacteria. It can be stated, as a general observation, that the ratio of biofilm bacteria to free water-born bacteria is more than 10:1. In many water delivery systems, the residence time of the water as it flows through the system may range from only a few seconds up to about one minute. If one employs the conventional approach of intermittently producing an antiseptic environment in a water delivery system, there will remain the potential for regrowth and replenishment of bacteria by the remaining biofilm bacteria because of their resistance to most biocides, resulting in an unacceptably high bacterial count in the water delivered to the patient. By eliminating the mature biofilm through a constant supply of an effective potable biocide, this major source of contamination is eliminated. By increasing the contact time of the biocide through the use of a mixing chamber, newly introduced water-born and patient-originated bacteria are greatly reduced in number or eliminated depending upon the contact time.

The present invention provides a process by which mature biofilms, including biofilms of the type produced by gram negative bacteria such as *Pseudomonas aeruginosa*, are reduced to the point of elimination through the use of a hydroxycarboxylic acid in relatively low concentrations so as not to be harmful to human tissue. As will be discussed in greater detail below, the preferred bactericidal agents for use in the present invention are low molecular weight hydroxycarboxylic acid, such as glycolic acid, lactic acid, malic acid, tartaric acid, and citric acid. Especially preferred are the hydroxypolycarboxylic acids, such as malic, tartaric and citric acids. Citric acid is particularly preferred because of its availability, low cost, and confirmed general safety. As indicated by the experimental data presented hereinafter, citric acid at a low concentration, e.g. about 0.1 wt. %, is effective not only in preventing the formation of biofilms, but in actually eliminating mature biofilms. It is also, at this same low concentration, capable of rapidly killing both water and human-originated pathogenic bacteria. While not required, much higher concentrations can be used without harmful side effects.

While, as indicated by the experimental work described later, the present invention is effective in the elimination of mature biofilms commonly encountered in water supply systems regardless of their bacterial genesis, the bacterium *Pseudomonas aeruginosa* is a highly ubiquitous bacterium, and this species will be used in broadly describing the invention as the standard for determining the activity of the preferred hydroxycarboxylic acid bactericide. In carrying out the invention, water supplied to a dental patient is treated with a hydroxycarboxylic acid bactericide in an amount sufficient to eliminate a mature biofilm produced by *Pseudomonas aeruginosa* bacteria. By using *Pseudomonas aeruginosa* as the standard for treatment, effective biofilm elimination can be achieved regardless of the particular bacterial species involved. The presence of the mature biofilm can be eliminated to the point where the predominant bacteria content in the water is free water-born bacteria as contrasted with biofilm bacteria. Stated otherwise, the replenishment mechanism noted above is interdicted so that the bacterial content, if any, is mostly free bacteria.

Turning now to FIG. 1, there is illustrated a schematic illustration of one embodiment of the present invention. The embodiment in FIG. 1 is specifically adapted for the supply of water to a dental unit which may be of any type, such as will be well known to those skilled in the art. Referring further to FIG. 1, there is illustrated a water supply line 10 which is adapted to be connected to any suitable source of water. For example, supply line 10 may be connected to a tap for the supply of city water, or it may be connected to a special water source. The line 10 preferably is provided with a relatively fine filter 12 to filter out suspended sediments. Preferably, the water filter is at least a 50-micron filter, i.e. one that functions to filter out particulates having an average particle size of 50 microns or more. In a preferred application of the invention for use in dental units, the filter may take the form of a 25-micron filter, that is, a filter permitting the passage only of particulates of a size of 25 microns or smaller.

In the case where municipal water and the like is involved, the water supply line is provided with a pressure reducing valve 16 which functions to reduce the line pressure to a desired value. For example, municipal water supplies typically involve line pressures ranging from about 45 to 100 psi (absolute), whereas if, as is preferred, a peristaltic pump is employed to incorporate bactericide into the water, it is desirable to provide a substantially lower pressure in order to provide for efficient operation of the pump. In this case, the pressure-reducing valve will function to reduce the line pressure to about 18 to 22 psia.

The output from the pressure-reducing valve is applied through a check valve 18 to a mixing junction 20 which provides for the incorporation of the citric acid or other bactericidal agent into the water supply line. A variable rate pump 22 is connected through a pump inlet line 24 to a reservoir 23 which contains a suitable bactericidal agent, for example a 15 wt. % aqueous solution of citric acid. Calcium saccharin or sodium saccharin can be added in a 1 wt. % quantity to the citric acid solution to make the final delivered water mixture more palatable if the application is dental or other similar use. An outlet line 26 from the pump provides a bactericide supply line to the mixing junction 20.

A flow sensing unit 28 is incorporated into the water supply line. Sensing unit 28 may incorporate a flow meter of any suitable type which generates an output signal representative of the sensed flow rate. The flow sensor produces an output signal which is applied via channel 27 to a microprocessor 29 which controls the speed or the volumetric pumping rate of the pump 22 by means of a control circuit 25. Preferably, the flow sensing unit 28 is located downstream of the mixing junction as shown. By locating the sensing unit here, rather than at a point in the supply line prior to the supply of bactericide, the tendency of biofilm production in the flow sensing unit will be alleviated. This is because the bactericide will also prevent biofilm formation on the flow sensor or flow switches. As described later, the sensing unit preferably will take the form of two or more incremental "flow switches." Preferably, these flow switches will be formed of 316 grade stainless steel or FDA grade plastic or any other suitable material which is not adversely affected by the presence of a relatively concentrated citric acid solution. A check valve 30 is located in the water supply line downstream of the flow sensor, and it likewise should be formed of a material such as is not adversely affected by a high citric acid environment. By way of example, the fittings for the sensor and the check valve could be formed of nylon or polypropylene. The check valve can take the form of a polypropylene ball having a crack pressure of ½ psi and biased to the closed position by a high grade stainless steel spring.

Figure 3:
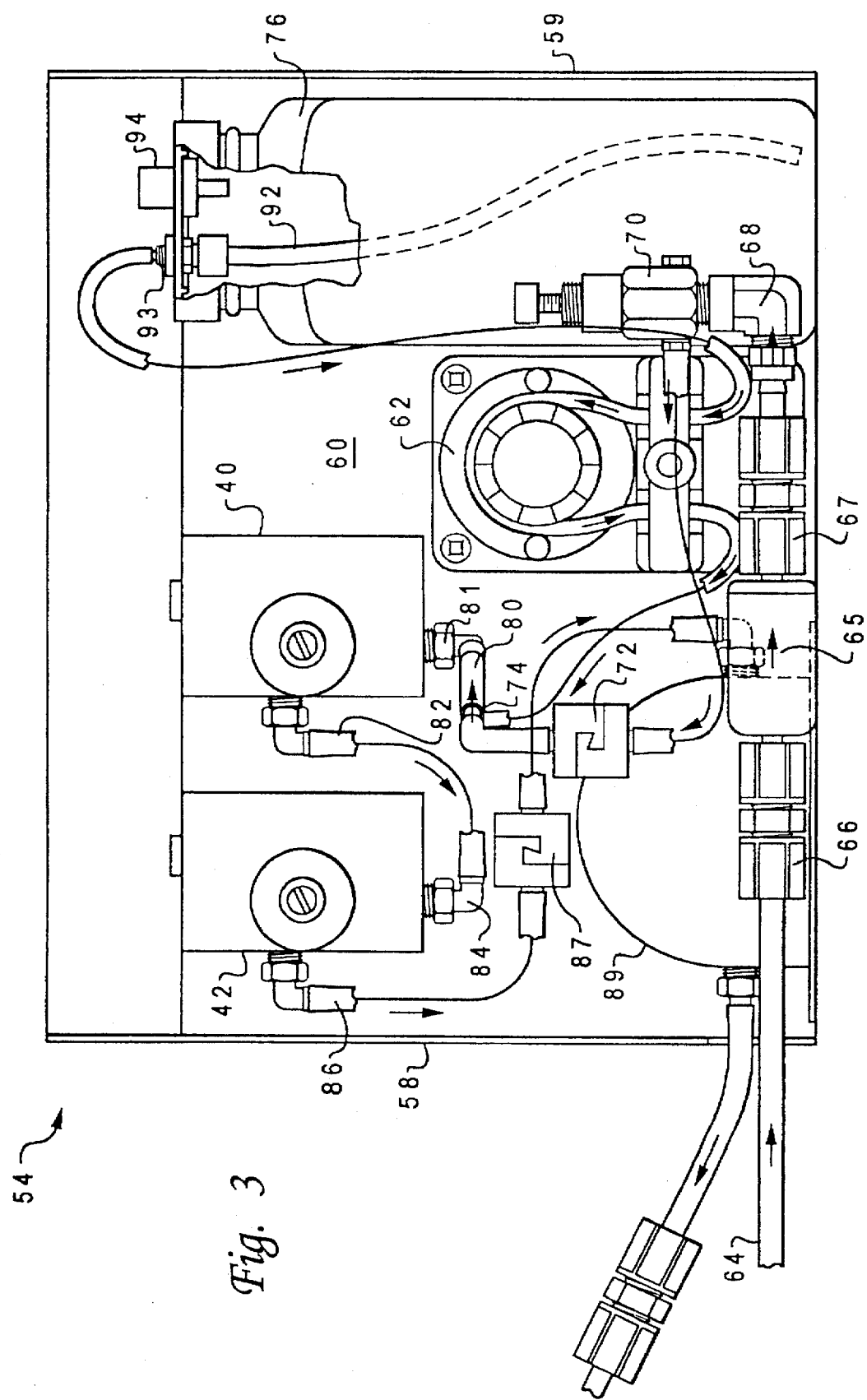
FIG. 3 is a side elevation with parts broken away showing an embodiment of the invention incorporated into a portable water sanitizing unit adapted for use in dental systems.

The fluid output from the sensing unit 28 is applied via check valve 30 and line 32 to an enlarged mixing chamber 34. The mixing chamber 34 functions to ensure a properly mixed treated water supply and to allow a volume of water to be treated over time to allow the bactericide to work prior to being delivered. An outlet line 35 from the surge chamber 34 extends to a suitable fitting 36 which is adapted to be connected to an endpoint utilization device. In the preferred embodiment of the invention, as described below, the outlet line 35 is connected to a dental unit 37 which may be equipped with any suitable utensils for use in dentistry. Suitable dental appliances which may be employed in conjunction with the dental unit include drill turbines, drill motors, air/water syringes, irrigators, sonic and ultrasonic scalers, endodontic ultrasonic and sonic filers, etc. The dental unit 37 comprises one or more water delivery lines to which the dental appliances can be releasibly connected. Water will be supplied to the various dental appliances at rates which can vary substantially from one applicance to the next. In the embodiment of FIG. 3, the dental unit 37 is shown schematically to incorporate a drill unit 37a and a syringe 3b. These hand pieces can be attached to the end of a water delivery line 38 by means well known to those skilled in the art. For a further discussion of dental units of the type which may employed in carrying out the present invention, reference is made to U.S. Pat. No. 5,360,338 to Waggoner and also the aforementioned U.S. Pat. No. 5,158, 454 to Viebahn et al., the entire disclosures of which are incorporated herein by reference. The flow sensing unit can be of any suitable type which functions to produce either an analog or digital output signal representative of flow rate through the line. Preferably, the sensing unit comprises a plurality of series connected flow-measuring devices which can have a variable signal output in relation to the measured flow rate, an incremental output in response to the flow rate reaching a designated level or a combination of such flow-measuring units, for example, having one incremental output and the other a variable output. Preferably, however, the sensing unit takes the form of a plurality of series connected incremental flow switches, which are used in conjunction with a peristaltic pump which is operated by a variable speed DC motor.

Figure 2:
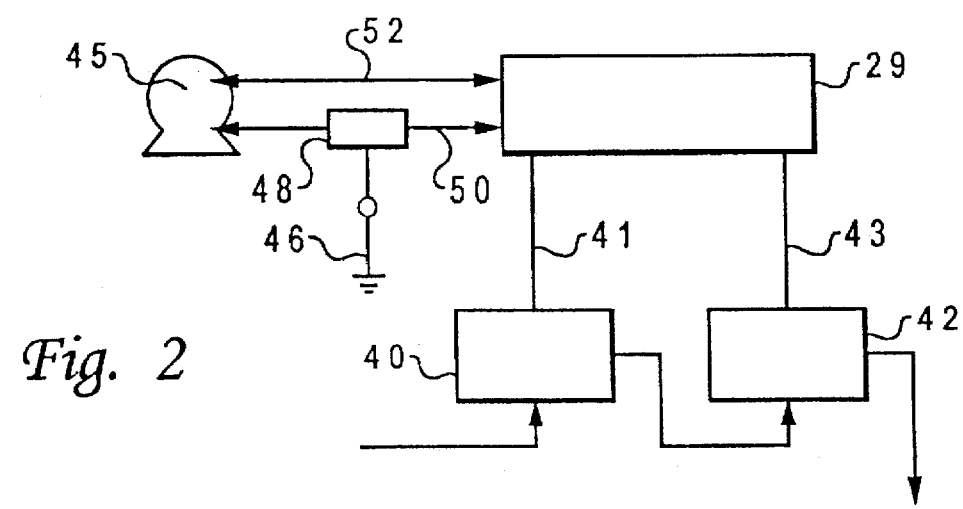
FIG. 2 is a schematic illustration of an embodiment of the invention incorporating sequential flow switches in order to monitor flow rate.

A system incorporating this preferred embodiment of the invention is illustrated in FIG. 2. Here, the flow sensing unit comprises a plurality of incremental flow switches operating at different flow rates. For example, in the embodiment illustrated in FIG. 2, two flow switches indicated by reference numerals 40 and 42 are involved—one operating at a flow rate of 3 ml per minute and the other operating at a flow rate of 24 ml per minute. Thus, the flow switches 40 and 42 may each take the form of an adjustable flow monitor available from Chem. Tec under the model designated 125BP. These flow switches, which are made of stainless steel, are characterized by a magnetic piston which is forced into proximity to a reed switch to actuate the switch at a given flow rate. When the flow rate falls below the designated set point, the piston moves out of proximity and the switch is deactivated. The microprocessor 29 operates to vary the pump speed and therefor the pumping rate in response to the output from the flow switches 40 and 42. Thus, by way of example, the pump motor 45 is energized from a 12-volt DC source 46 through a pump motor controller 48 which controls the voltage applied to the motor, and thus the motor speed. For example, at a first flow rate of 3 ml per minute, switch 40 is actuated to send a signal via channel 41 to microprocessor 29. The microprocessor responds to generate a command signal via channel 50 to apply a low voltage, e.g. 1.4 VDC, to operate the motor of the variable speed peristaltic pump to provide a pump rate of 0.2 ml of bactericide solution. When the flow rate reaches 24 ml per minute, switch 42 is activated, sending a signal via channel 43 to the microprocessor 29. The microprocessor responds by sending a signal to motor control unit 48 to step up the voltage to increase the pump speed to pump 1.2 ml per minute of bactericide to the flow line at the mixing junction. A signal, representative of the speed of the pump, is applied via channel 52 to the microprocessor 29 so that the feedback control is provided to maintain the pump at the designated speed. The feedback control may be accomplished by any suitable means, such as a magnetic pickup or a photoelectric cell used to measure pump speed. For example, a slotted disk may be mounted on the shaft of the pump and located between an electro-optic transducer and a source of light so that the transducer output produces a signal directly representative of the speed of the pump. This signal is processed by the microprocessor and any adjustments made as necessary to vary the voltage to the voltage variable motor of the peristaltic pump to ensure that the pump runs at the proper speed associated with the outputs from the flow switches.

As indicated previously, variable output sensing units can be employed. One or both of the flow switches 40 and 42 may be replaced by a sensing unit operating over a designated range to provide a variable output signal. Where one of the flow monitors operates to produce a variable output proportional to flow rate, it usually will be preferred to employ this unit in place of flow switch 42 to sense a variable flow rate over a relatively high range; for example, a range of 10-20 milliliters per minute. Preferably the control system is integrated so that the higher flow-rate monitor having a variable output functions only after the control system receives the incremental signal function representative of the flow rate at a designated lower range. The signal appearing at channel 52 may also be employed to provide a fail-safe feature which shuts down the pump in the event the pump operates for more than a designated time period. For example, the microprocessor can be provided with an internal clock which is driven to a time-out function in response to a signal appearing continuously on channel 52 indicating uninterrupted operation of the pump. Should this signal be present for a period which would be beyond the operating time expected during normal operation, e.g. one hour, the clock function will act to apply a signal via channel 50 to open the circuit to voltage source 46 and thereby shut down the motor. This also activates an alarm such as a buzzer or other audio or visual signal generators which would act to alert the operator. The system cannot thereafter be restarted without the application of an external reset signal. For example, the microprocessor may be programmed so that it cannot be restarted until power is completely removed from the unit and thereafter applied. For example, where the system voltage is supplied by a 12-volt transformer connected to a 120 or 220 AC voltage source, as is commonly employed for office use, the system may be reset by simply unplugging the transformer.

From the foregoing description, it will be recognized that the present invention is directed not only to sanitizing the supplied water but, more importantly, to destroying or preventing the formation of bacterial biofilm on surfaces within the water supply unit. By maintaining continuously an atmosphere which is antagonistic to the formation of the biofilm, the overall bacterial contamination within the water can be kept at an acceptably low level. Thus, the invention departs from the normal prior art approach to bacterial contamination in that it is aimed not so much at destroying bacteria within the water, but instead destroying or reducing the biofilm from which bacteria may emanate. This important feature of the invention enables the water to have a very low level of bacteria through the use of relatively mild bacterial agents, i.e. bactericidal agents which are not irritant to or destructive to tissue and which can be tolerated, if necessary, under conditions involving relatively long exposures and can be consumed, if necessary, without harm.

Although only two flow switches are illustrated in the embodiment of FIG. 2, it will be recognized that three or more flow switches can be provided in the event it is desired to exercise closer control of the pump speed in relation to the amount of bactericide introduced into the supply line in response to the water supply flow rate. For example, three switches could be employed, set to produce output signals at two ml per minute, 16 millimeters per minute, and 50 ml per minute. In either case, the peristaltic pump can be driven by a 12-volt DC variable speed motor with the motor RPM's directly proportional to the voltage amplitude supplied to the motor.

Also while an incremental mode of operation is provided by two or more constant flow switches having incremental set points is preferred, it is to be recognized that an analog control scheme can be employed. For example, rather than step-wise operation of the pump motor, the flow rate can be continuously monitored to a relatively close tolerance and the motor speed varied to maintain the concentration of the citric acid or other bactericide at a relatively constant level within the water supply line. This application is useful where large water volume variations are required or closer tolerances are necessary. In a dental application, a system incorporating the two or more flow switch approach is the preferred configuration.

Figure 4:
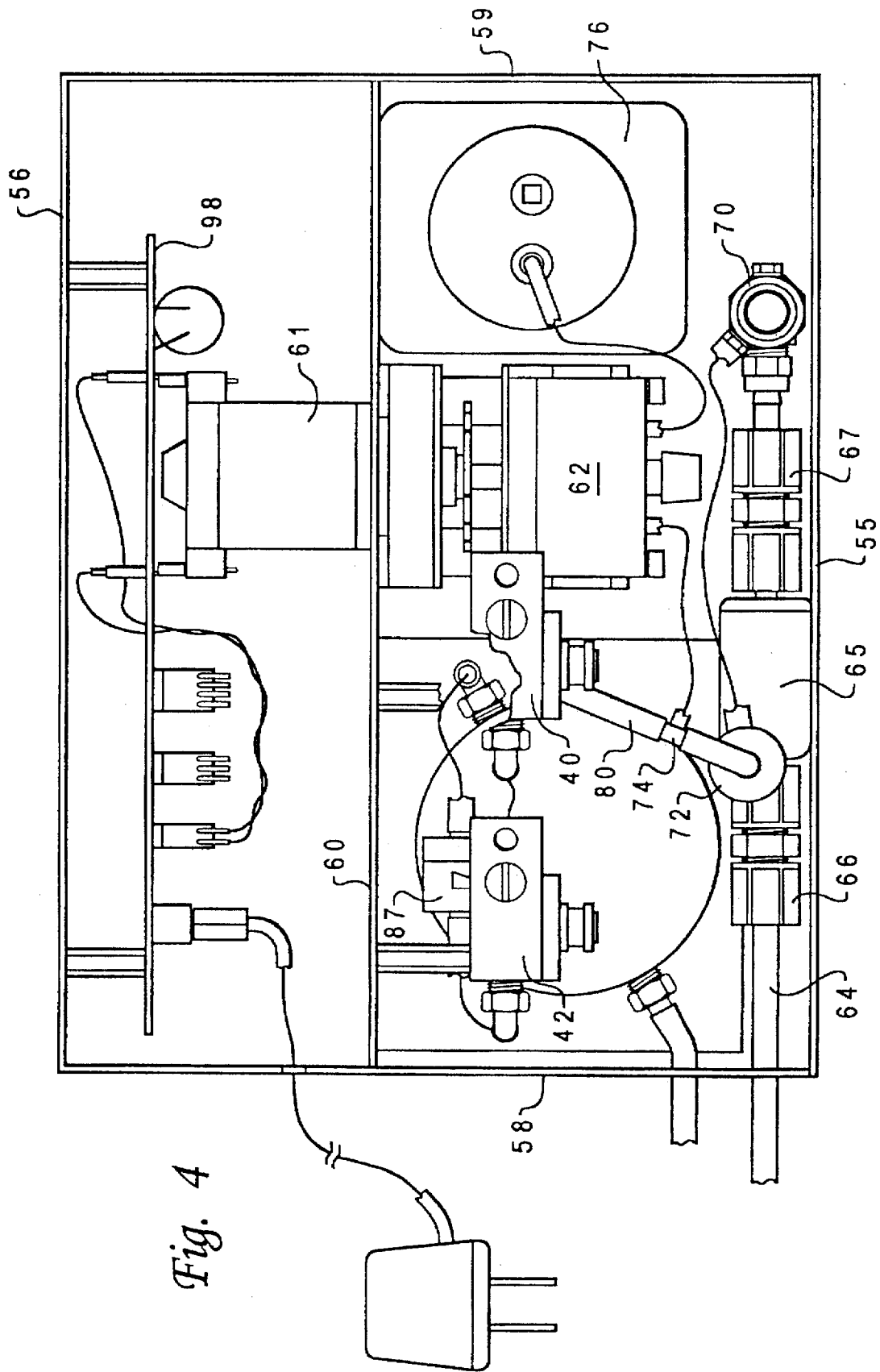
FIG. 4 is a plane view of the system shown in FIG. 3.

FIGS. 3 and 4 illustrate a water sanitizing unit adapted for use with dental units and the like. FIG. 3 is a side elevation with parts broken away of the sanitizing unit; FIG. 4 is a top view of the system shown in FIG. 3. Turning first to FIG. 3, there is illustrated a side elevation with parts broken away of a water sanitizing unit adapted for use with dental units and the like. More particularly and as shown in FIGS. 3 and 4, the sanitizing unit is mounted within a container 54, having front and back walls 55 and 56 and side walls 58 and 59. A transverse intermediate partition 60 extends between the side walls and provides a mounting surface for a peristaltic pump 62 and its drive motor 61 and a pair of variable speed incremental flow switches 40 and 42.

As further shown in FIG. 3, a water inlet line 64 of clear polyurethane tubing extends through an in-line 25-micron water filter 65 held in place by in-line compression fittings 66 and 67, respectively. Arrows (→) are used for line 64 and various other conduits shown in FIG. 3 to indicate flow direction. The output line from the compression unit 67 is applied to a brass elbow fitting 68 which leads into the bottom of a pressure-reducing valve 70. Valve 70 reduces the water line pressure to a suitable value, e.g. 18 pounds per square inch. The outlet line from valve 70 passes to an in-line polypropylene check valve 72 which has a one-half psi cracking pressure. This valve is provided with buna-N rubber seals and a 316 grade stainless steel spring so that it is not subject to corrosive action by the citric acid or other hydroxycarboxylic acid. The output line from the check valve 72 extends into a ⅛-inch tubing "T" 74 provided with a side line having an ID of 1/16 inch. This, of course, provides a mixing junction for a water solution of bactericide supplied from a reservoir 76 via peristaltic pump 62. The output line 80 from the mixing junction 74 extends to an elbow 81 at the bottom of the first flow switch 40. The output from flow switch 40 is applied through an exit elbow and an interconnecting flow line 82 through elbow 84 to the bottom of the second flow switch 42. The output of flow switch 42 is applied through an exit elbow and PVC flow line 86 to a one-way check valve 87, again having a crack pressure of ½ psi, to the bottom of a mixing chamber 89, which preferably has a capacity within the range of 50–250 ml. Mixing chamber 89 preferably takes the form of a dome-shaped tank having a flat bottom and a capacity of about 125 cc.

The reservoir 76 for the bactericide may take the form of a one-liter polypropylene bottle which is removably contained within the enclosure 54. The bottle 76 is closed with an airtight cap 91 which serves as a mount for a collection tube 92 running to the bottom of the bottle from a bulkhead nipple 93 and an air filter 94. The filter 94 may take the form of a 0.2 micro hydrophobic syringe filter which provides for venting of the reservoir 76 as bactericide is withdrawn. The filter could be of a 0.45 micron configuration or larger as long as it is hydrophobic in nature. The output end of the collector tube is connected to a 1/32-inch I.D. Norprene (Norton) tubing which runs to the inlet side of the peristaltic pump 62 and vents from the outlet side of the pump to the inlet of the mixing junction, "T" 74.

The pump motor and the switch outlets are connected to a controller 98 board which incorporates an integral motor control unit and microprocessor mounted on the back wall 56 of the container 54. Power may be supplied to the controller by a wall mounted step-down transformer having a 12-volt AC output which can then be rectified to DC voltage in the controller board.

With the exception of the reservoir 76, which is removable, the other components of the system are firmly mounted within the container 54 to provide an integral unit. The reservoir can be removed in order to readily replenish the bactericide when the supply has been exhausted and to ensure the bactericide does not spill on essential components.

As noted previously, gram-negative bacteria are the most common source of slime layer buildup within water supply lines leading to dental units and the like. The most commonly encountered bacteria are Pseudomonas species. The effectiveness of citric acid as a biocide for water-originated biofilms has been tested and established by the following experimental work. *Pseudomonas aeruginosa* was chosen for the experimental work due to its high prevalence and high resistance and the fact that it produces one of the heaviest biofilms. The test used a 24-hour culture of *Pseudomonas aeruginosa* (ATCC 9027) grown in tryptic soy broth which was inoculated into 100 milliliter polyvinylchloride bottles containing 50 milliliters of sterile water U.S.P. (Baxter). The inoculum was determined to produce a concentration of $1.88 \times 10^6$ per milliliter of *Pseudomonas aeruginosa* per bottle. These bottles were stored at room temperature and agitated every 12 hours. After 10 weeks a mature biofilm should have been produced. Twelve bottles were utilized for this aspect of the study. Three were control bottles, and these had their volumes replaced with sterile water U.S.P. (Baxter). The next three bottles were designated "A," and their volume was replaced with a solution of citric acid in tap water at a concentration of 0.14 wt. %. The third group of three bottles was designated "B," and their volume was replaced with a tap water/citric acid concentration of 0.117 wt. %. The fourth group of three bottles was designated "C," and their volume was replaced with a tap water/citric acid concentration of 0.117 wt. %, plus 0.7 grams of Sweet-n-Low saccharine sweetener was added to a concentration of 0.0084 wt. % calcium saccharin. The saccharin was added to make the water/citric acid mixture more palatable.

The three control bottles had about 20,000,000 CFU per milliliter for each of the bottles at this 10-week timeframe. All twelve bottles were tested at 1 day, 3 days, and 7 days. At days 1, 3, and 7 all the treated bottles showed no growth. The three control bottles showed an immediate growth, presumably from their biofilm, of 270,000–430,000 CFU per milliliter on day one, 410,000–510,000 CFU per milliliter on day three, and 270,000–490,000 CFU per milliliter on day seven.

At the end of the seven days, all the bottles containing the citric acid mixture were emptied completely and filled with 10% trypile soy growth broth in sterile water U.S.P. These were allowed to incubate at 37° C. for 48 hours and then were removed from the incubator and incubated an additional 5 days at room temperature. After 7 days, samples were taken from each of the bottles and plated on tryptic soy broth with lecithin and tween. No growth was seen. This experimental work showed:

(1) The presumed presence of a viable biofilm, (2) The rapid inactivation of the biofilm using a very dilute citric acid solution in a very short period of time, (3) The total destruction of biofilm at the end of 7 days, and (4) That addition of calcium saccharin had no detrimental effects of the citric acid's effectiveness.

Another separate study was performed to determine the rate and size of reduction of pathogenic bacteria that two different citric acid concentrations were able to accomplish. The three bacteria chosen have all been observed in dental unit waterlines and are all ATCC so they are assured of purity. Two are of human origin and one of water origin.

Two citric acid/tap water concentrations were prepared. Sample "A" contained a 0.467 wt. % concentration of citric acid and sample "B" had a citric acid concentration of 0.233 wt. %. Both of these samples contained 0.24% calcium saccharin. Into sterile test tubes containing either of these samples were placed either *Escherichia coli* in a concentration of 160,000,000 CFU per milliliter, *Staphylococcus aureus* in a concentration of 190,000,000 CFU per milliliter, and *Pseudomonas aeruginosa* in a concentration of 140,000, 000 CFU per milliliter. These samples were tested at 10 minutes, 30 minutes, 60 minutes, and 24 hours.

For the *Escherichia coli*, sample A showed a complete kill at 10 minutes. For sample B, a reduction down to 6 CFU per milliliter was seen at 30 minutes. It took more than 60 minutes but less than 24 hours to completely eliminate the *E. coli* with sample B.

For the *Staphylococcus aureus*, sample A showed a complete kill at 30 minutes. For sample B, a reduction down to 2,000 CFU per milliliter was seen at 60 minutes and a complete kill was seen at 24 hours. For the *Pseudomonas aeruginosa*, sample A and sample B showed a complete kill at 10 minutes.

The effectiveness of the present invention can be considered in light of standards recognized by the U.S. Food and Drug Administration (FDA) for delineating sterile conditions. The FDA recognizes a 6 log ($10^6$) reduction of bacteria as a confirmation for reaching sterility. Against this background, it can be seen that the foregoing experimental work establishes that a larger reduction of bacteria can be achieved at low concentrations of citric acid standardly delivered by the water sanitizing system of the present invention during typical dental operations, such as drilling and utilization of an ultrasonic scaler. At least a 7 log reduction for *E-coli* and *Pseudomonas aeruginosa* was observed at ten minutes with concentrations of citric acid as described above with reference to samples "A" and "B." A 6 log reduction of *Staphylococcus aureus* was established at the 0.467 wt. % concentration at 30 minutes while a 5 log reduction was observed at the lower concentration (0.233 wt. %) at 60 minutes. A complete kill of all test bacteria was confirmed at 24 hours. In view of the 9 log reduction of both gram positive and gram negative bacteria at 24 hours, the potential for newly-introduced bacteria to produce a biofilm would appear to be very remote. In addition, the presence of saccharin, specifically calcium saccharin in the citric acid solution did not appear to adversely affect the function of the bactericide.

As indicated by the foregoing experimental work, the hydroxycarboxylic acid need be supplied in only relatively low concentrations in order to eliminate the formation of biofilm in the dental unit and the associated water supply lines and utilization devices. For the preferred low molecular weight hydroxycarboxylic acids employed in the present invention, a concentration of 0.1 wt. % is sufficient so long as the bactericide is supplied in a concurrent fashion in accordance with the present invention. Thus the bactericide concentration, as employed in the dental unit and the associated water supply lines, is preferably within the range of 0.1–1.0 wt. %. While greater amounts can be used, they are unnecessary and may offer objectionable bitterness to the patient. As a practical matter, during the majority of dental procedures, the concentration will be within the range of about 0.2 to about 0.8 wt. %. This range is dictated by the ratio of the pump speed to the delivered water flow rate relative to each of the flow switches' activation points. This concentration range is targeted because it offers both the ability to destroy bacterial biofilms as well as the ability to rapidly destroy newly introduced bacteria, and it can do this at very palatable concentrations. As discussed above, the water supply rates can vary widely from one dental instrument to another. The large mixing chamber allows higher and lower concentrations to be mixed so that these concentrations can be averaged. This mixing chamber also acts as a treatment holding tank so that the hydroxycarboxylic acid may act upon the newly treated water prior to delivery. As a practical matter, the concentration of citric acid, or other hydroxypolycarboxylic acid, usually will be near the upper end of the aforementioned range only when extremely hard water with substantial alkaline earth metal compounds such as calcium and magnesium chlorides and carbonates are encountered. A more preferred concentration will be within the range of about 0.2 to about 0.5 wt. % during most of a cycle of operation. As noted previously, the water supply rates can vary widely depending upon the particular dental instrument used and low concentrations outside of the aforementioned ranges can be tolerated especially at low flow rates as long as there is some compensation provided by concentrations within the desired range. For example, if it is desirable giving considerations of water hardness and the like to maintain a bactericide concentration of at least 0.2 wt. %, intermittent concentrations below this value can be tolerated so long as overall the concentration is within the desired range of 0.2–0.5 wt. %. An important consideration in this invention is that so long as the bactericide is supplied to the dental unit water in a concurrent fashion, i.e., continuously or nearly continuously with only small interruptions, biofilm formation will be largely prevented and any biofilm that does form, e.g., because of inactivity of the system, will be effectively eliminated.

Having described specific embodiments of the present invention, it will be understood that modifications thereof may be suggested to those skilled in the art, and it is intended to cover all such modifications as fall within the scope of the appended claims.

What is claimed:

1. In a system for incorporating a bactericide into an aqueous medium for supply to a water distribution unit, the combination comprising:

(a) a reservoir adapted to contain a liquid bactericidal agent;

(b) a variable rate pump having an inlet line extending from said reservoir to the inlet of said pump;

(c) an outlet line extending from the outlet of said pump and providing a bactericide supply line;

(d) a water supply line adapted to be connected to a source of water under pressure at a water inlet and providing a water supply flow path through said system to an outlet of said water supply line adapted to be connected to a utilization unit;

(e) a mixing junction for said water supply line and said bactericide supply line to provide for mixing of a bactericide into said water supply line;

(f) a flow-sensing unit responsive to fluid flow in said water supply line to generate an output parameter representative of the flow rate in said water line; and (g) a flow control system for controlling the pumping rate of said pump in response to said measured parameter.

2. The system of claim 1 further comprising an enlarged mixing chamber between said mixing junction and said water supply line outlet.

3. The combination of claim 2 wherein said mixing junction is upstream of said sensing unit.

4. The combination of claim 3 wherein said sensing unit is interposed between said mixing chamber and said mixing junction.

5. The combination of claim 2 wherein said pump is a positive displacement pump.

6. The combination of claim 5 wherein said positive displacement pump is a peristaltic pump.

7. The combination of claim 1 wherein a check valve is located in said water supply line upstream of said mixing junction.

8. The combination of claim 7 further comprising a water filter in said water supply line between said inlet and said mixing junction.

9. The combination of claim 8 wherein said water filter is at least a 50-micron filter.

10. The combination of claim 1 wherein said sensing unit comprises a plurality of series connected flow monitors which operate to produce signal outputs representative of different rates of flow.

11. The combination of claim 10 wherein one of said monitors comprises a flow switch operative to produce an incremental signal function in response to a first flow rate and another of said monitors comprises a variable flow sensor operative to produce a variable signal function having a variable output proportional to a sensed variable flow rate.

12. The combination of claim 11 wherein said flow control system is enabled to control said pump in response to said variable signal function only after receiving said incremental signal function.

13. The combination of claim 11 wherein said flow control system controls the pumping rate at said pump in direct relationship to the supply water flow rate as determined by the variable flow sensor.

14. The combination of claim 1 wherein said control system comprises a fail-safe internal clock function which acts to shut down the pump in response to continuous operation of said pump in excess of a designated time limit.

15. The combination of claim 14 wherein the control system comprises means responsive to the shut down of said pump by activation of the fail-safe function, to generate an audio alarm will sound to alert an operator that the water sanitizer is not functioning.

16. The combination of claim 1 wherein said sensing unit comprises a plurality of series-connected flow switches, a first of said flow switches being operative to produce a signal function in response to a first flow rate and a second of said flow switches being operative to produce a signal function in response to a second flow rate greater than said first flow rate.

17. The combination of claim 16 wherein the pump operates at first rate of speed when the first flow switch is actuated and a higher rate of speed when the second flow switches are actuated.

18. The combination of claim 1 wherein said system is incorporated into a portable self-contained unit capable of being moved from one location to another by hand and wherein said reservoir is removably contained within said unit.

19. The combination of claim 1 further comprising first and second check valves in said water supply line, said first check valve being disposed in said line upstream of said mixing junction and said second check valve being disposed downstream of said mixing junction, with said sensing unit being interposed between said mixing junction and said second check valve.

20. The combination of claim 19 further comprising an enlarged mixing chamber in said water supply line interposed between said second check valve and said outlet adapted to be connected to a dental unit.

21. The combination of claim 20 wherein said sensing unit comprises a plurality of series-connected flow switches, a first of said flow switches being operative to produce a signal function in response to a first flow rate and a second of said flow switches being operative to produce a signal function in response to a second flow rate greater than said first flow rate.

22. The combination of claim 21 wherein said pump is a positive displacement pump.

23. The combination of claim 22 wherein said positive displacement pump is a peristaltic pump.

24. In a dental station for the treatment of dental patients, the combination comprising:
  (a) a dental system having at least one dental appliance and at least one water supply line for delivering water to a selected one of said appliances;
  (b) a sanitizing unit comprising a reservoir adapted to contain a liquid bactericidal agent and a variable rate pump having an inlet line extending from said reservoir to the inlet of said pump and an outlet line extending from the outlet of said pump providing a bactericide supply line;
  (c) a water supply line adapted to be connected to a source of water under pressure at a water inlet point and providing a water supply flow path through said sanitizing unit to an outlet connected to said dental unit to provide a supply of water to said dental unit;
  (d) a mixing junction for said water supply line and said bactericide supply line to provide for mixing of a bactericide into said water supply line;
  (e) an enlarged mixing chamber in said water supply and interposed between said mixing junction and said dental unit;
  (f) a flow-sensing unit responsive to fluid flow in said water supply line to generate an output parameter representative of the flow rate of said water supply line; and
  (g) a flow control system for controlling the pumping rate of said pump in response to said measured parameter.

25. The combination of claim 24 wherein said sensing unit is interposed between said mixing chamber and said mixing junction.

26. The combination of claim 25 wherein a check valve is located in said water supply line upstream of said mixing junction.

27. The combination of claim 26 wherein said positive displacement pump is a peristaltic pump.

28. In a method for providing a sanitized aqueous medium to a dental unit, the steps comprising:
  (a) providing a dental unit for use in dental treatment;
  (b) delivering water to said dental unit from a water source; and
  (c) incorporating into said water a hydroxycarboxylic acid in bactericidally-effective amount sufficient to eliminate the presence of a mature biofilm produced by *Pseudomonas aeruginosa* bacteria.

29. The method of claim 28 where the hydroxycarboxylic acid is a polycarboxylic acid.

30. The method of claim 29 wherein said acid is selected from the group consisting of malic acid, tartaric acid, and citric acid.

31. The method of claim 30 wherein said hydroxycarboxylic acid is citric acid.

32. The method of claim 31 wherein said citric acid is mixed with a non-nutritive sweetener.

33. The method of claim 31 wherein said citric acid is supplied to said water to provide an average concentration in said water within the range of 0.1–1.0 wt. %.

34. In a method for providing a sanitized aqueous medium to a dental unit, the steps comprising:
  (a) providing a dental unit for use in treatment applied within a patient's mouth;
  (b) supplying a stream of water to said dental unit and applying said water from said dental unit into the patient's mouth;

(c) incorporating into said water supplied to said dental unit a hydroxycarboxylic acid in a bactericidally-effective amount sufficient to eliminate a mature biofilm produced by *Pseudomonas aeruginosa* bacteria;

(d) sensing the flow rate of water supplied to said dental unit; and (e) adjusting the rate of incorporation of said hydroxycarboxylic acid into said water in response to said sensed flow rate.

35. The method of claim 34 wherein said water is filtered to remove suspended sedimentary material from said water prior to incorporation of said hydroxycarboxylic acid into said water.

36. The method of claim 35 wherein said water is filtered to remove sedimentary material having an average particle size greater than 50 microns.

37. The method of claim 36 wherein said water is filtered to remove suspended sedimentary material in a particle size greater than 25 microns.

38. The method of claim 34 wherein said hydroxycarboxylic acid is a polycarboxylic acid.

39. The method of claim 38 wherein said acid is selected from the group consisting of malic acid, tartaric acid, and citric acid.

40. The method of claim 39 wherein said hydroxycarboxylic acid is citric acid.

41. The method of claim 40 wherein said citric acid is supplied to said water to provide an average concentration in said water within the range of 0.1–1.0 wt. %.

42. The method of claim 40 wherein said citric acid is mixed with a non-nutritive sweetener.

43. The method of claim 34 further comprising the step of sequentially employing a plurality of dental unit end devices and supplying said water to each of these said dental units from a central sanitizing station.

44. In a method for providing dental treatment the steps comprising:

(a) providing a dental unit having a plurality of appliances associated therewith and at least one water delivery line for delivering water to said appliances;

(b) supplying water to said dental unit and through a water supply line to a first selected hand piece while concurrently incorporating into said water supply to said dental unit a hydroxycarboxylic acid in a bactericidally-effective mount sufficient to eliminate a mature biofilm produced by *Pseudomonas aeruginosa* bacteria;

(c) terminating the flow of water to said dental unit;

(d) selecting a second of said hand pieces and supplying water to said dental unit and through a water supply line to said second hand piece at a flow rate different from the flow rate of step (b) while concurrently incorporating into said water supply to said dental unit a hydroxycarboxylic acid in a bactericidally-effective amount sufficient to eliminate a mature biofilm produced by *Pseudomonas aeruginosa* bacteria;

(e) adjusting the rate of incorporation of said hydroxycarboxylic acid into said water to provide a different rate of incorporation during step (d) than the rate of incorporation during step (b).

45. The process of claim 44 wherein said hydroxycarboxylic acid is incorporated into said water supply by mixing a concentrated solution of said hydroxycarboxylic acid with water flowing through said water supply line.

46. The process of claim 45 wherein said hydroxycarboxylic acid is a polycarboxylic acid.

47. The method of claim 46 wherein said hydroxycarboxylic acid is citric acid.

48. The method of claim 47 wherein citric acid is supplied to said water supply line to provide a concentration in said water supply line with the range of 0.1–1.0 wt. %.

* * * * *